(12) United States Patent
Bayston et al.

(10) Patent No.: US 6,191,306 B1
(45) Date of Patent: Feb. 20, 2001

(54) PROCESS FOR THE PREPARATION OF CYCLOPROPYLGLYCINE

(75) Inventors: Daniel John Bayston, Oxfordshire; Jonathan Luke William Griffin, Reading, both of (GB); Arne Gruman, Malmo (DE); Mario Eugenio Cosimino Polywka, Abingdon Oxon; Ronald Michael Scott, Oxfordshire, both of (GB)

(73) Assignee: Eastman Chemical Company, Kingsport, TN (US)

( * ) Notice: Under 35 U.S.C. 154(b), the term of this patent shall be extended for 0 days.

(21) Appl. No.: 09/365,914

(22) Filed: Aug. 3, 1999

(51) Int. Cl.$^7$ ................................................... C07C 227/18
(52) U.S. Cl. ............................ 560/124; 558/315; 560/38; 564/275
(58) Field of Search ..................... 560/124, 38; 558/315; 564/275

(56) References Cited

U.S. PATENT DOCUMENTS 3,987,178  * 10/1976  Fosker et al. ........................ 424/271

* cited by examiner

*Primary Examiner*—Peter O'Sullivan
(74) *Attorney, Agent, or Firm*—Michael J. Blake; Harry J. Gwinnell

(57) ABSTRACT

Disclosed is a process for the preparation of cyclopropylglycine by a 5-step process wherein cyclopropanecarboxaldehyde is reacted with an α-aminoalkylaromatic compound to obtain an imine which is reacted with a cyanide to produce an aminonitrile compound; the aminonitrile compound is hydrolyzed to the corresponding aminocarboxylic acid and finally the arylalkyl residue is removed from the amino group by hydrogenolysis.

5 Claims, No Drawings

PROCESS FOR THE PREPARATION OF CYCLOPROPYLGLYCINE

This invention pertains to a process for preparing cyclopropylglycine (CPG) including racemic and substantially enantiomerically pure (R) or (S)-CPG. More specifically, this invention pertains to a process for the preparation of CPG by a 5-step process wherein cyclopropanecarboxaldehyde (CPCA) is reacted with an a-aminoalkylaromatic compound to obtain an imine which is reacted with a cyanide to produce an aminonitrile compound; the aminonitrile compound is hydrolyzed to the corresponding aminocarboxylic acid and finally the arylalkyl residue is removed from the amino group by hydrogenolysis. The present invention also includes certain of the individual process steps and intermediate compounds.

Unnatural amino acids are an important class of organic compounds and often are found in physiologically active compounds. Similarly, the cyclopropyl fragment also is found in pharmaceutical products. See, for example, U.S. Pat. No. 3,474,101, U.S. Pat. No. 3,433,791, Published PCT Patent Application WO 9304047, Spanish Patent ES 539110, U.S. Pat. No. 4,863,918, Czech Patent CZ 279821 and European Patent Publication EP 0380312 A1.

The synthesis of racemic CPG first was reported by Lowry, *J. Am. Chem. Soc.,* 1952, 1355 in a 9% yield using Strecker chemistry. Whitesides, *J. Am. Chem. Soc.,* 111, 6354 (1989) describes the preparation of homochiral CPG by enzymatic resolution of racemic CPG. This resolution has been performed on a millimole scale, presumably because of the difficulty in preparing racemic CPG. U.S. Pat. No. 3,987,178 (1976) discloses D-, L- and DL-CPG and methods for the preparation and resolution thereof. One method for the preparation of DL-CPG starts with CPCA which is converted to CPG via cyclopropyl-5-hydantoin. Another method involves the reaction of bromocyclopropane with diethyl acetamido sodiomalonate. The resolution of DL-CPG also is disclosed in U.S. Pat. No. 3,987,178 by the enzymatic hydrolysis of the acetamide of CPG using Hog Kidney Acylase I.

The use of chiral a-methylbenzylamine as an auxiliary in Strecker-type synthesis of other compounds is disclosed in U.S. Pat. No. 3,914,249; Synth. Commun., 1986, 16, 337; J. Org. Chem., 1983, 48, 5369; Helc. Chim. Acta., 1979, 62, 956; Helv. Chim. Acta., 1980, 63, 824; J. Org. Chem., 1989, 54, 1055. In no case was a cyclopropylcarbonyl substrate used.

We have developed a process for the preparation of both racemic and substantially enantiomerically pure (R) or (S)-CPG beginning with CPCA. Our novel process comprises the steps of:

(1) contacting CPCA with an amine having the formula

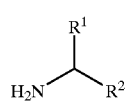

(I)

in the presence of a solvent comprising an alkanol, water or a mixture thereof to obtain an imine having the formula:

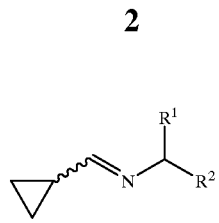

(II)

(2) contacting the imine of formula (II) with a cyanide selected from alkali metal, alkaline earth metal and trimethylsilyl cyanides in the presence of a solvent comprising an alkanol, water or a mixture thereof to obtain an aminonitrile compound having the formula:

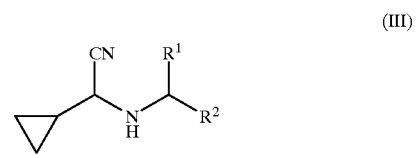

(III)

(3) contacting the aminonitrile compound of formula (III) with a strong acid in the presence of water to obtain an acid addition salt of an aminocarboxylic acid having the formula:

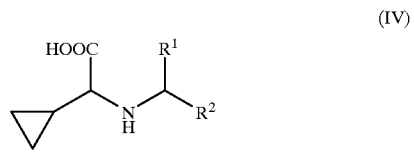

(IV)

(4) contacting the acid addition salt of the aminocarboxylic acid of formula (IV) with a hydroxide, carbonate or bicarbonate of an alkali metal or alkaline earth metal in the presence of water to obtain the free aminocarboxylic acid of formula (IV); and (5) contacting the aminocarboxylic acid of formula (IV) with hydrogen in the presence of a hydrogenation catalyst and an inert solvent to obtain CPG;

wherein $R^1$ is hydrogen or an alkyl radical, e.g., unsubstituted or substituted $C_1$–$C_3$ alkyl; and $R^2$ is a carbocyclic aryl radical. The use of highly enantiomerically pure (>99% enantiomeric excess [ee], where enantiomeric excess is defined as the percent of one enantiomer minus the percent of the other enantiomer) (R) or (S) amine (I) wherein $R^1$ is alkyl and $R^2$ is phenyl, substituted phenyl, or naphthyl gives the corresponding substantially enantiomerically pure CPG (for the purposes of this invention, substantially enantiomerically pure indicates a compound possessing >95% ee) whereas the use of racemic or achiral amine (I) in which $R^1$ is alkyl, aryl, or hydrogen and $R^2$ is phenyl, substituted phenyl, or naphthyl gives racemic CPG. CPG is useful in the preparation of pennicillins as is disclosed in U.S. Pat. No. 3,987,178 (1976).

Our novel process also includes the novel intermediate compounds produced and utilized in the above-described process, i.e., imine (II), aminonitrile (III) and aminocarboxylic acid (IV).

In the first step of the process, amine (I) is reacted with CPCA in the presence of an inert solvent to produce imine (II). The inert solvent preferably is an alkanol, e.g., an alkanol containing about 1 to 4 carbon atoms, water or an alkanol/water mixture. The first step may be carried out at a temperature in the range of about room temperature up to the boiling point of the solvent, preferably at a temperature of about 50 to 70° C. The mole ratio of CPCA:amine (I) normally will be about 0.75:1 to 1.25:1. Imine (II) produced in step (1) may be isolated, e.g., by standard extraction techniques known in the art, but preferably is used in step (2) in the form of the reaction product mixture obtained from step (1).

The alkyl radicals which $R^1$ may represent may be unsubstituted $C_1$–$C_3$ alkyl such as methyl, ethyl and propyl or $C_1$–$C_3$ alkyl substituted with groups such as hydroxy; halogen, e.g., chloro and bromo; nitro; or mercapto. The carbocyclic aryl radical represented by $R^2$ may be unsubstituted or substituted phenyl or naphthyl. Examples of the substituents which may be present on the phenyl and naphthyl radicals which $R^2$ represent include alkyl, e.g., $C_1$–$C_4$ alkyl; alkoxy, e.g., $C_1$–$C_4$ alkoxy; halogen, e.g., chloro and bromo; nitro; hydroxy; and the like. Normally, the phenyl and naphthyl radicals will not be substituted by more than 2 of any such substituents. The amine having formula (I) preferably is α-methylbenzylamine or benzylamine, the latter useful only for racemate preparation.

The second step of the process comprises contacting imine (II) obtained from the first step with a cyanide reactant in the presence of an inert solvent, typically the same solvent as that which is used in the first step. The cyanide reactant may be selected from one or more alkali metal, alkaline earth metal or trimethylsilyl cyanides, preferably an alkali metal cyanide such as potassium or sodium cyanide. The second step may be carried out at a temperature in the range of below room temperature up to the boiling point of the solvent, preferably at a temperature of about 15 to 45° C. The mole ratio of cyanide reactant:imine (II) normally will be about 1:1 to 10:1.

When amine (I) is a substantially enantiomerically pure compound, i.e., (R) or (S) amine (I) wherein $R^1$ is alkyl, the process of step 2 is unexpectedly observed to proceed with >2:1 diastereoselectivity. For example, when $R^1$ is methyl and $R^2$ is phenyl, the addition of cyanide to imine (II) is observed to provide aminonitrile (III) in a 3.2:1 ratio of diastereomers. The major diastereomer possesses either the (R,R) configuration [starting with the (R)-amine] as shown in IIIa or the (S,S) configuration [starting with the (S)-amine] as shown in IIIb. The minor diastereomer in each case possesses the (S,R) configuration as shown in IIIc and IIId. This diastereoselectivity is unexpected and could not be predicted, but is advantageous for the preparation of substantially enantiomerically pure CPG.

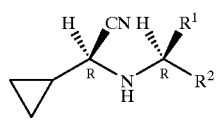

(IIIa)

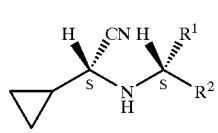

(IIIb)

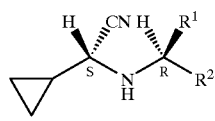

(IIIc)

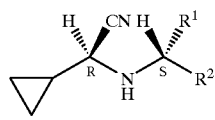

(IIId)

Thus, a second embodiment of the process of the present invention involves a process for the preparation of an aminonitrile having the formula

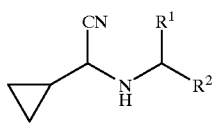

(III)

which comprises the steps of:

(1) contacting CPCA with a substantially enantiomerically pure amine having the formula (I)

$$H_2N\underset{R^2}{\overset{R^1}{\diagdown}}$$

in the presence of a solvent comprising an alkanol, water or a mixture thereof to obtain an imine having the formula:

(II)

(2) contacting the imine of formula (II) with a cyanide selected from alkali metal, alkaline earth metal and trimethylsilyl cyanides in the presence of a solvent comprising an alkanol, water or a mixture thereof to produce aminonitrile (III);

wherein $R^1$ is an alkyl radical, e.g., unsubstituted or substituted $C_1$–$C_3$ alkyl; $R^2$ is a carbocyclic aryl radical; and aminonitrile (III) consists of a mixture of diastereomers with the ratio of major to minor diastereomers of greater than 2:1, preferably greater than 3:1. The major diastereomer possesses either the (R,R) configuration [starting with the (R)-amine] as shown in IIIa or the (S,S) configuration [starting with the (S)-amine] as shown in IIIb. The minor diastereomer in each case possesses the (S,R) configuration as shown in IIIc and IIId.

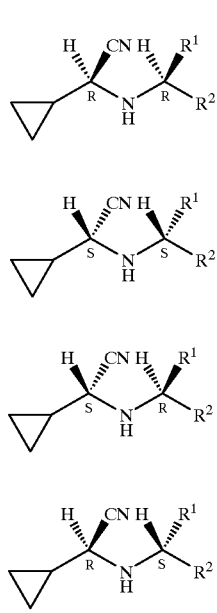

(IIIa)

(IIIb)

(IIIc)

(IIId)

In the third step of the process, the aminonitrile of formula (III) from step (2) is contacted with a strong acid in the presence of water to hydrolyze the aminonitrile to the corresponding aminocarboxylic acid. Examples of suitable strong acids include non-oxidizing mineral acids such as hydrohalic acids such as hydrochloric and hydrobromic acids; sulfuric acid; phosphoric acid; alkyl- and arylsulfonic acids such as methanesulfonic, benzenesulfonic and toluenesulfonic acids. The strong acid preferably is hydrochloric acid. The strong acid:aminonitrile (III) mole ratio normally is at least 1:1 and more typically is in the range of about 8:1 to 14:1. Step (3) may be carried out at a temperature of about 50 to 100° C., preferably about 90 to 100° C. The reaction product produced by step (3) is the acid addition salt of aminocarboxylic acid (IV), e.g., the hydrochloride or sulfate of aminocarboxylic acid (IV).

The acid addition salt of aminocarboxylic acid (IV) produced in step (3) is treated with a base in step (4) to convert the amine salt to the free amine. The base may be selected from one or more of the hydroxides, carbonates and/or bicarbonates of the alkali metals and/or alkaline earth metals. Sodium and potassium hydroxides are the preferred bases. Steps (3) and (4) preferably are carried out without isolating the acid addition salt of aminocarboxylic acid (IV) produced in step (3), usually in the same vessel. The amount of base used in step (4) can be varied significantly, e.g., an amount which will impart to the reaction mixture a pH in the range of 1 to 12. It is preferred, however, that the amount of base utilized will give a reaction mixture having a pH of about 5 to 10 and, most preferably a pH in the range of about 7 to 9 to obtain optimum recovery of aminocarboxylic acid (IV). Surprisingly, the neutralization of the acid addition salt affords selective precipitation of the major diastereomer. The major diastereomer possesses either the (R,R) configuration as shown in IVa [starting with the (R)-amine] or the (S,S) configuration as shown in IVb [starting with the (S)-amine] Thus, the diastereomeric excess is improved from about 50% to >95%. Washing the precipitate with a lower alcohol or water further enhances the diastereomeric excess to >98%.

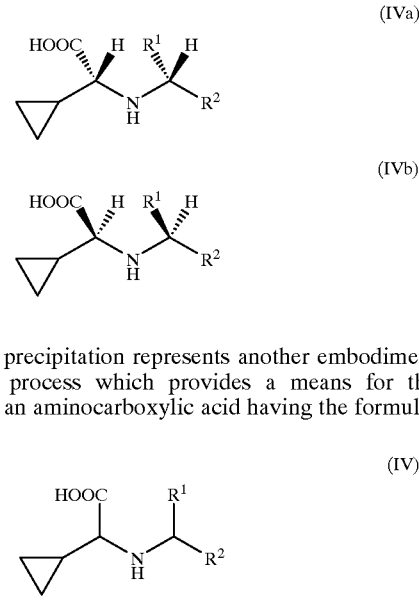

(IVa)

(IVb)

This selective precipitation represents another embodiment of our novel process which provides a means for the preparation of an aminocarboxylic acid having the formula:

(IV)

by contacting an aqueous solution of an acid addition salt of aminocarboxylic acid of formula (IV) with a hydroxide, carbonate or bicarbonate of an alkali metal or alkaline earth metal in the presence of water to obtain a precipitate of the free aminocarboxylic acid of formula (IV); wherein $R^1$ is an alkyl radical, e.g., unsubstituted or substituted $C_1$–$C_3$ alkyl; $R^2$ is a carbocyclic aryl radical; and the free aminocarboxylic acid of formula (IV) consists of greater than 97.5 mole percent of the major diastereomer.

In step (5) of the process of the present invention, aminocarboxylic acid (IV) is subjected to a conventional hydrogenolysis treatment to remove the arylalkyl residue of the aminocarboxylic acid and thereby produce CPG. The hydrogenolysis treatment of step (5) comprises contacting a solution of aminocarboxylic acid (IV) in an inert solvent, preferably an alkanol, e.g., an alkanol containing about 1 to 4 carbon atoms, water or an alkanol/water mixture, with hydrogen or a suitable hydrogen donor of such as formic acid and a hydrogenation catalyst. The hydrogenation catalyst may be selected from the metals of Group VIII and compounds thereof, e.g., nickel, palladium, platinum and the like. The catalyst preferably comprises a supported palladium or platinum catalyst, e.g., catalysts comprising about 2 to 20 weight percent, preferably 5 to 10 weight percent, palladium or platinum deposited on a catalyst support material. Palladium and palladium hydroxide on carbon are particularly preferred hydrogenation catalysts.

The process described herein may be carried out at ambient pressures. However, pressures moderately below or above ambient pressure may be used in one or more of the steps of the process. For example, increased pressure may permit the use of higher reaction temperatures and/or may provide for enhanced contact of process materials, e.g., hydrogen contact in the hydrogenolysis of step (5). In particular, hydrogen pressures for step 5 can be in the range of 1 to 100 atmospheres, preferably 1 to 30 atmospheres.

The operation of the process and preparation of the novel compounds provided by our invention are further illustrated by the following example. Gas chromatographic (GC) analyses were performed on a Hewlett-Packard 5890 series 11 gas chromatography with a 30 meter DB-Wax and a 30 meter DB-17 capillary columns. The identities of the products obtained were confirmed by nuclear magnetic spectrometry and gas chromatography-mass spectrometry by comparison to authentic samples. The percentages specified in the examples are by weight unless otherwise specified.

EXAMPLE1

CPCA (175 g, 2.5 mol) was dissolved in methanol (1.751, 10 vol) and (S)α-methylbenzylamine (322 mL, 2.5 mol) was added. The resulting solution was heated at reflux for 1.5 hours and then cooled to 30° C. After the addition of potassium cyanide (162.8 g, 2.5 mol), the reaction mixture warmed to 32° C. without external cooling. The heterogeneous mixture was stirred overnight and water (580 mL, 3.3 vol) was added to dissolve all of the potassium cyanide. Concentrated hydrochloric acid (200 mL, 1.1 vol) and 2N hydrochloric acid (40 mL, 0.2 vol) were added to adjust the pH of the reaction mixture to 10. Water (1.8 L, 10 vol) was added whereupon the reaction mixture separated into two phases. The aqueous top layer was extracted with ethyl acetate (3×0.7 L, 12 vol) and the extracts were dried over magnesium sulfate and filtered. The filtrates were combined with the bottom layer from the above two-phase mixture and evaporation of volatiles in vacuo gave the aminonitrile of formula (III) [$R^1$=methyl, $R^2$=phenyl] as a yellow oil (489 g, 98% yield). The product was obtained as a 3.2:1 [(S,S):(R,S)] ratio of diastereomers.

The crude aminonitrile from the procedure of the preceding paragraph (10 g, 0.05 mol) was dissolved in concentrated hydrochloric acid (65 mL, 6.5 vol) and heated to and maintained at 94° C. for 17 hours. 4N potassium hydroxide (175 mL, 17.5 vol) was added slowly to the black reaction mixture between room temperature and approximately 50° C. until the pH was 8-9. The now beige mixture was cooled in an ice bath with stirring for 45 minutes. The solid which formed was filtered, washed with ice cold water (50 mL, 5 vol) and then slurried in ice cold methanol (100 mL, 10 vol) for 10 minutes. After filtering, the white solid was washed with methanol (2×50 mL) and dried on the filter paper and then in a vacuum oven to give aminocarboxylic acid (IV) [$R^1$=methyl, $R^2$=phenyl] (5.98 g, 55% of theory, >99% diastereomeric excess by HPLC).

The aminocarboxylic acid prepared according to the preceding paragraph (1 g) was added to 10 weight percent palladium on carbon (50% water wet, 0.3 g, 14% w/w) in methanol (20 mL, 20 vol). The resulting mixture was stirred at room temperature under an atmosphere of hydrogen for 48 hours. The catalyst was removed by filtration. The filtrate was concentrated in vacuo to give a white solid which was dried to constant weight at the freeze dryer to give (R)-CPG (IV) [$R^1$=methyl, $R^2$=phenyl] as an off-white solid (0.16 g, 31% of theory). The palladium catalyst was slurried in water (50 mL, 50 vol) at 90° C. for 30 minutes. The catalyst was again removed by filtration and filtrate concentrated in vacuo to give a white solid which was dried to constant weight at the freeze dryer to give (S)-CPG (0.30 g, 57% of theory; total 88% yield).

EXAMPLE 2

A 20 liter flange flask was set up with a mechanical stirrer, thermometer, dropping funnel, condenser and nitrogen inlet and outlet (to a bleach scrubber). Water (8.2 L) and cyclopropylcarboxaldehyde (1 equivalent, 1.64 kg, 1.75 L) were added and stirring commenced. Benzylamine (1.05 equivalents, 2.63 kg, 2.68 L) was added at a rate so as to keep the temperature below 30° C. After stirring for 3 hours at room temperature, potassium cyanide (1.05 equivalents, 1.6 kg) was added and then stirred a further 2 hours. The pH was adjusted to pH 10 by the addition of concentrated hydrochloric acid, giving a 2 layer system. The phases were separated and the aqueous phase extracted with tertiary butyl methyl ether (3×1.75 L). The combined organic extracts were washed with brine (10 L) and the volatiles removed in vacuo to leave the aminonitrile as a pale yellow oil (4.27 kg, 99%).

A heating mantle and flange flask was set up with a mechanical stirrer, thermometer, dropping funnel, condenser and nitrogen inlet and outlet (to a bleach scrubber). The crude aminonitrile from above (1 equivalent, 1.46 kg) was added and stirring commenced. Concentrated HCl (7.28 L) was added and the mixture heated at 100° C. for 2 hours after which time 1H NMR indicated that the reaction was complete. The reaction mixture was cooled to room temperature and acetone (7.28 L) added. The resulting precipitate was collected on filter paper, washed with acetone (2× 1.92 L) and dried in vacuo to give amino acid hydrochloride salt. The HCl salt was dissolved in water (8.17 L) and the pH adjusted to 7–8 by the addition of 4M aqueous NaOH. The precipitated solid was collected on filter paper, washed with acetone (2×2.5 I) and dried in vacuo to give the N-benzylamino acid as a white solid (1.05 kg, 65%).

A slurry of N-benzylamino acid (prepared as above) (0.7 kg) in methanol (8.4I, 12 vol) was added to 5% palladium on carbon (50% water wet, 0.35 kg, 50% w/w) under nitrogen. The resulting mixture was purged with hydrogen by 3 vacuum/hydrogen sequences and stirred vigorously at 50° C. under an atmosphere of hydrogen for 2.5 hours. After cooling to room temperature, the catalyst was removed by filtration. The filtrate was concentrated in vacuo to give a white solid (A). The palladium catalyst was slurried in water (2×3.5 L, 2×5 vol) at 90–100° C. for 30 min. The catalyst was again removed by a hot filtration, solid A added to the filtrate and to the cooled (room temperature) filtrate acetone (5.6 L, 8 vol) was added. The resulting precipitate was then allowed to stir for 30 minutes, and then filtered off. The residue was washed with acetone (2×4I, 2×2 vol), then dried in vacuo to give racemic cyclopropylglycine as a white solid (0.285 kg, 73% yield).

The invention has been described in detail with particular reference to preferred embodiments thereof, but it will be understood that variations and modifications can be effected within the spirit and scope of the invention.

We claim:
1. Process for the preparation of cyclopropylglycine (CPG) which comprises the steps of:

(1) contacting cyclopropanecarboxaldehyde with an amine having the formula

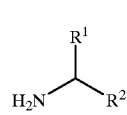

(I)

in the presence of a solvent comprising an alkanol, water or a mixture thereof to obtain an imine having the formula:

(II)

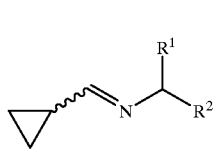

(2) contacting the imine of formula (II) with a cyanide selected from alkali metal, alkaline earth metal and trialkylsilyl cyanides in the presence of a solvent comprising an alkanol, water or a mixture thereof to obtain an aminonitrile compound having the formula:

(III)

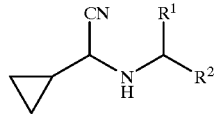

(3) contacting the aminonitrile compound of formula (III) with a strong acid in the presence of water to obtain an acid addition salt of an aminocarboxylic acid having the formula:

(IV)

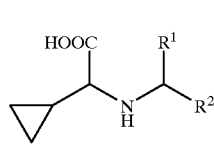

(4) contacting the acid addition salt of the aminocarboxylic acid of formula (IV) with a hydroxide, carbonate or bicarbonate of an alkali metal or alkaline earth metal in the presence of water to obtain the free aminocarboxylic acid of formula (IV); and (5) contacting the aminocarboxylic acid of formula (IV) with hydrogen or a hydrogen donor in the presence of a hydrogenation catalyst and an inert solvent to obtain CPG; wherein $R^1$ is hydrogen or an alkyl radical; and $R^2$ is a carbocyclic aryl radical.

2. Process according to claim 1 which comprises the steps of:
(1) contacting cyclopropanecarboxaldehyde with an amine having the formula (I)

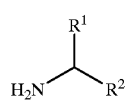

in the presence or a solvent comprising an alkanol, water or a mixture thereof at a temperature of about 50 to 70° C. to obtain an imine having the formula:

(II)

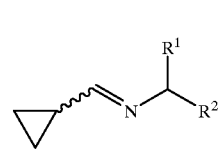

(2) contacting the imine of formula (II) present in a reaction mixture produced in step (1) with a cyanide selected from sodium and potassium cyanides to obtain an aminonitrile compound having the formula:

(III)

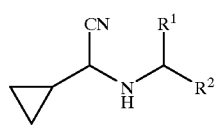

3. Process according to claim 2 which comprises the steps of:
(3) contacting an aminonitrile compound of formula (III) with a strong acid in the presence of water to obtain an acid addition salt of an aminocarboxylic acid having the formula:

(IV)

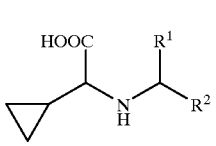

(4) contacting the acid addition salt of the aminocarboxylic acid of formula (IV) present in a reaction mixture obtained from step (3) with sodium or potassium hydroxide to obtain the free aminocarboxylic acid of formula (IV); and (4) contacting the aminocarboxylic acid of formula (IV) with hydrogen or a hydrogen donor in the presence of a palladium or platinum hydrogenation catalyst and an inert solvent to obtain CPG.

4. Process according to claim 1 wherein amine (I) is a highly enantiomerically pure (R) or (S)-amine having the formula (I)

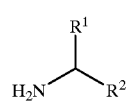

wherein $R^1$ is $C_1$–$C_3$ alkyl or $C_1$–$C_3$ alkyl substituted with hydroxy, halo, nitro, or mercapto; and $R^2$ is a carbocyclic aryl radical.

5. Process according to claim 4 wherein $R^1$ is methyl and $R^2$ is phenyl.

* * * * *